United States Patent [19]
Alden et al.

[11] Patent Number: 5,730,752
[45] Date of Patent: Mar. 24, 1998

[54] TUBULAR SURGICAL CUTTERS HAVING ASPIRATION FLOW CONTROL PORTS

[75] Inventors: Donald L. Alden, Sunnyvale; Jeffrey J. Christian, San Jose, both of Calif.

[73] Assignee: FemRx, Inc., Sunnyvale, Calif.

[21] Appl. No.: 738,643

[22] Filed: Oct. 29, 1996

[51] Int. Cl.⁶ ................................................. A61B 17/14
[52] U.S. Cl. ................................................. 606/180; 604/35
[58] Field of Search ......................... 606/35–50, 80, 606/167, 180; 604/19, 22, 35, 902; 128/749–754

[56] References Cited

U.S. PATENT DOCUMENTS

| | | | |
|---|---|---|---|
| 3,945,375 | 3/1976 | Banko. | |
| 4,517,977 | 5/1985 | Frost. | |
| 5,186,714 | 2/1993 | Boudreault et al. | 604/35 |
| 5,217,479 | 6/1993 | Shuler | 606/180 |
| 5,226,910 | 7/1993 | Kajiyama et al. | 606/171 |
| 5,248,297 | 9/1993 | Takase | 606/22 |
| 5,336,167 | 8/1994 | Sullivan et al. | 604/22 |
| 5,366,468 | 11/1994 | Fucci et al. | 606/180 |
| 5,403,317 | 4/1995 | Bonutti | 606/180 |
| 5,437,630 | 8/1995 | Daniel et al. | 604/22 |
| 5,456,689 | 10/1995 | Kresch et al. | 606/180 |

*Primary Examiner*—Glenn K. Dawson
*Attorney, Agent, or Firm*—Townsend and Townsend and Crew LLP

[57] ABSTRACT

The invention provides tubular surgical cutter devices which include aspiration flow control ports to enhance the ability of the cutter to remove severed tissues from an internal surgical site. The aspiration flow control ports will admit sufficient aspiration fluid to transport tissue fragments that are severed by the tubular surgical cutter through the lumen of the cutter, even when the severing aperture is entirely blocked by a target tissue. The aspiration flow control ports will typically be in one of two forms. In the first form, a vacuum relief port provides open fluid communication with the lumen of the tubular cutter when the cutting aperture is open to receive target tissues for severing. In the second form, a fenestration pattern through an outer tube of the cutter ensures that aspiration flow continues even when the cutting aperture of the outer tube is blocked. Ideally, both vacuum relief ports and fenestrations are provided so that aspiration flow is entrained into the lumen of the tubular cutter throughout the cutting stroke.

13 Claims, 5 Drawing Sheets

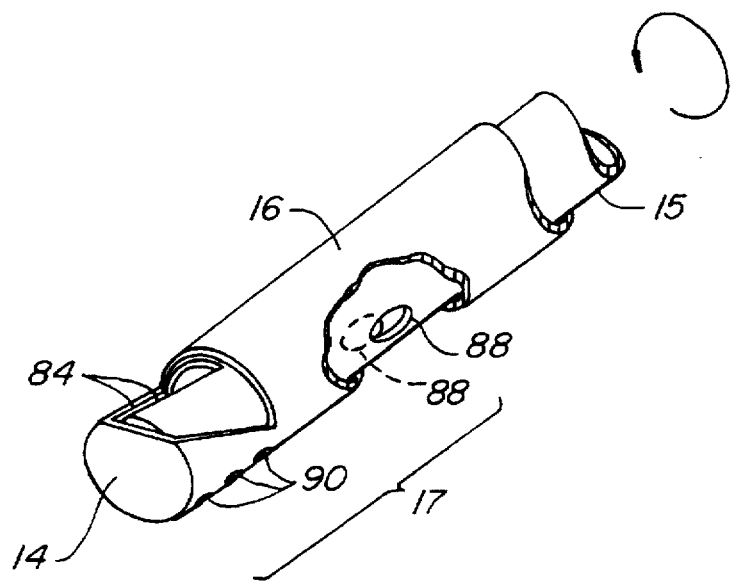
FIG. 4.
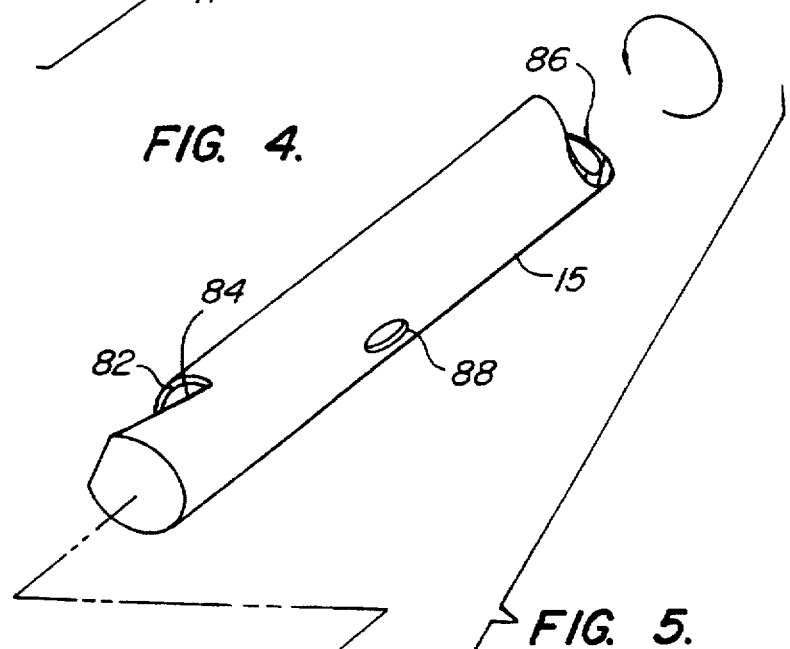
FIG. 5.
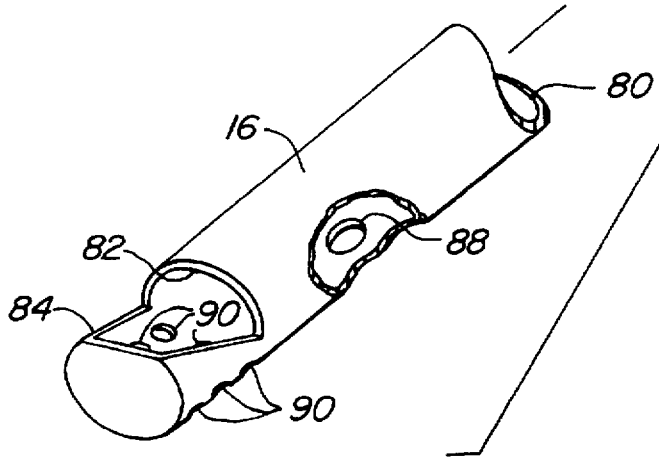

1

TUBULAR SURGICAL CUTTERS HAVING ASPIRATION FLOW CONTROL PORTS

BACKGROUND OF THE INVENTION

1. Field of the Invention

This invention relates generally to surgical cutting devices, and in particular, provides a tubular surgical cutter for use in internal tissue resection, endoscopy, arthroscopy, and other minimally-invasive surgical procedures, in which the cutter has aspiration flow ports to control the size and facilitate movement of tissue fragments aspirated into a lumen of the cutter.

Tubular surgical cutters have been in use for many years to sever and aspirate internal tissues. For example, arthroscopic surgery techniques often involve manipulating a cutting probe through a small incision. In arthroscopic knee surgery, the distal end of the probe is manually positioned against a tissue to be cut, typically against a meniscus in the knee joint, so that the portion of meniscus that is to be trimmed protrudes into an aperture formed in an outer tubular structure of the probe. An inner tubular structure rotates within this outer tubular structure, the inner tube often including a chopping edge which sweeps by the edge of the aperture of the outer tube. Hence, the meniscus (and any other tissues which protrude into the aperture) is sheared between the chopping edge of the inner tube and the edge on the outer tubular structure. The severed meniscus or other tissue may then be aspirated through a lumen of the inner tube for removal from the internal surgical site.

More recently, the use of tubular surgical cutters has been combined with electrosurgical tissue resection, particularly for trans-cervical fibroid removal. Prior to electrosurgical fibroid removal, the uterus is flooded with a nonconductive fluid, such as sorbitol-mannitol fluid or the like, under sufficient pressure to separate the walls of the uterus and render the surgical site suitable for optical fiber observation. This procedure is generally described as uterine cavity distension. During this flooding, an electrocautery surgical tool is inserted into the uterus through the cervix. Electrical current at high voltage settings (typically an alternating current of about 750 KHz and 2000–9000 volts) is transmitted from a cutting surface of the surgical instrument to the surgical site. The cutting surface usually consists of a wire or solid shape. The transmission of current to the uterus is monopolar, and the circuit is completed by a conductive path to the power unit through a conductive pad applied to the patient's skin.

The electrical current is concentrated at the cutting surface. Heat generated from the resistance of tissue to the flow of electrical current is high enough to vaporize cells near the cutting surface. Thus, a cut is made with very little physical resistance to the cutting motion. Heat from the cut also cauterizes small blood vessels so that visibility and control remain fairly good. However, a secondary effect of the removal of tissue, particularly in the area of fibroid removal, is that separated tissue fragments typically remain in the working area and must be periodically flushed or suctioned away to preserve the required visibility necessary for surgery.

U.S. patent application Ser. No. 08/136,426, filed Oct. 13, 1993, (Attorney Docket No. 16944-000100) the full disclosure of which is incorporated herein by reference, describes an exemplary resection method and device including a rotating cutting head which chops resected tissue into fragments, thereby facilitating the continuous evacuation of resected tissue through the electrosurgical probe while the tissue is being resected. U.S. patent application Ser. No. 08/322,680, filed Oct. 13, 1994, (Attorney Docket No. 16944-000110) which is also incorporated herein by reference, provides resection methods and devices including both a rotating chopping mechanism and an electrosurgical cutting wire. Such an electrosurgical cutting wire is particularly well-suited for removal of strips of tissue from the uterus, prostate, or other internal body cavities. The rotating chopping mechanism severs the strips of removed tissue into tissue fragments, allowing the electrosurgical cutting wire and rotating chopping mechanisms to be independently optimized for these two distinct operations.

Although the use of tubular surgical cutters for tissue morcellation and aspiration has proven to be highly effective, work in connection with the present invention has shown that known tubular cutter structures could benefit from still further improvements. Specifically, conventional tubular cutters intermittently direct the full aspiration vacuum toward the tissue to be resected when the apertures of the inner and outer tubular structures come into rotational alignment. This has been found to draw excessively large amounts of tissue into the cutter, particularly when soft tissues are being removed. Furthermore, when the inner and outer apertures are not aligned, the aspiration flow path is substantially closed off. The result is oversized tissue fragments and insufficient aspiration fluid flow, which can result in clogging of the aspiration path through the lumen of the inner cutter tube.

For the above reasons, it is desirable to provide improved clog resistant tubular surgical cutters and methods for their use. It would be particularly desirable if such tubular cutters limited the vacuum directed at the tissues being severed, particularly for use in cutting soft tissues. It would further be advantageous if these improved tubular surgical cutters provided a continuous flow of aspiration fluid to promote aspiration of the tissue fragments after they have entered the cutter lumen.

SUMMARY OF THE INVENTION

The present invention generally provides tubular surgical cutter devices which include aspiration flow control ports to enhance the ability of the cutter to remove severed tissues from an internal surgical site. Generally, the aspiration flow control ports will admit sufficient aspiration fluid to transport tissue fragments that are severed by the tubular surgical cutter through the lumen of the cutter, even when the severing aperture is entirely blocked by a target tissue. The aspiration flow control ports will typically be in one of two forms. In the first form, a vacuum relief port provides open fluid communication with the lumen of the tubular cutter when the cutting aperture is open to receive target tissues therein for severing. These vacuum relief ports will help to ensure that irrigation fluid is drawn into the lumen together with the target tissue, and to prevent the full force of the vacuum from drawing oversized tissue fragments in through the aperture. The vacuum relief port also prevents tissue from being drawn too deeply into the aperture before being severed. In the second form a fenestration pattern through an outer tube of the cutter ensures that aspiration flow continues even when the cutting aperture of the outer tube is blocked. Ideally, both vacuum relief ports and fenestrations are provided so that aspiration flow is entrained into the lumen of the tubular cutter throughout the cutting stroke. Such aspiration flow control features are particularly advantageous when combined with an electrosurgical cutting surface, as they promote morcellation and removal of large strips of severed tissue and avoid clogging.

In a first embodiment, the present invention provides a tubular surgical cutter comprising an outer tubular structure having a proximal end, a distal end, and a cutting edge which borders an aperture disposed near the distal end. A lumen is provided between the aperture and the proximal end, and at least one aspiration flow port is located near the distal end. An inner tubular structure is rotatably disposed within the lumen of the outer tube, the inner tube having a proximal end, a distal end, a lumen therebetween, and a cutting edge which cooperates with the cutting edge of the outer tube to sever tissue fragments which enter the aperture of the outer tube. The aspiration flow port is in at least intermittent fluid communication with the lumen of the rotating inner tube. The aspiration flow port admits sufficient aspiration flow to transport the severed tissue fragments proximally through the lumen of the inner tube when aspiration flow through the aperture is blocked.

To allow the aspiration flow control port to admit the required aspiration flow, the aspiration flow port will often be separated from the severing aperture of the outer tube, typically being disposed roughly radially opposite the aperture. This allows the physician to position the severing aperture against a target tissue of an internal surgical site without fear of the target tissue blocking all aspiration flow. The aspiration flow control ports may optionally comprise vacuum relief ports on the inner and outer tubes which align when the severing aperture is open, or may comprise a plurality of fenestrations through the outer tube which align with a severing aperture of the inner tube so that aspiration flow continues when the outer aperture is blocked by the inner tube structure, the aspiration flow control ports ideally comprising both of these advantageous structures.

In another aspect, the present invention provides a tubular surgical cutter comprising an outer tubular structure having a proximal end, a distal end, and a cutting edge which borders an aperture disposed near the distal end. A lumen is provided between the aperture and the proximal end, and a vacuum relief port is disposed near the distal end which is in fluid communication with the lumen. An inner tubular structure has a proximal end, a distal end, a cutting edge which borders an aperture disposed near the distal end, and a lumen between the aperture and the proximal end. The inner tubular structure also includes a vacuum relief port disposed near the distal end which is in fluid communication with the lumen. The inner tube is rotatably disposed within the lumen of the outer tube so that the cutting edges cooperate to sever tissue fragments which protrude into the apertures. The vacuum relief ports are separated from the apertures and align with each other when the apertures are aligned to draw fluid into the lumen of the inner tube along with the tissue fragments.

In another aspect, the present invention provides a tubular surgical cutter comprising an outer tubular structure having a proximal end, a distal end, a cutting edge which borders an aperture near the distal end, and a lumen between the aperture and the proximal end. A plurality of fenestrations are disposed near the distal end, the fenestrations in fluid communication with the lumen. An inner tubular structure has a proximal end, a distal end, and an aperture. A cutting edge is disposed near the distal end, while a lumen is between the aperture and the proximal end. The inner tube is rotatably disposed within the lumen of the outer tube so that the cutting edges cooperate to sever tissue fragments which protrude into the aperture of the outer tube. The fenestrations align with the aperture of the inner tube when the inner tube blocks flow through the aperture of the outer tube. This allows fluid to be drawn into the lumen of the inner tube after the tissue fragments have been severed, thereby promoting transportation proximally of those severed tissue fragments.

In yet another aspect, the present invention provides a method for removing tissue from an internal surgical site. The method comprises irrigating the site with fluid and aspirating fluid from the site by drawing the fluid into an aperture and through a lumen of a tube. A target tissue at the site is protruded into the aperture and severed by rotating an inner cutting edge within the tube. Sufficient fluid is drawn into the lumen through an aspiration port of the tube to transport the severed tissue fragment proximally through the lumen of the tube, even when fluid flow through the aperture is blocked by the target tissue.

BRIEF DESCRIPTION OF THE DRAWINGS

FIG. 4 is a perspective view of the distal end of the tubular cutter of the probe of FIG. 1, in which a portion of the outer tube is removed to show the vacuum relief ports and the fenestrations which enhance transportation of severed tissue fragments proximally through the lumen of the inner tube.

FIG. 5 is an exploded view of the inner and outer tubes of FIG. 4.

DETAILED DESCRIPTION OF THE SPECIFIC EMBODIMENTS

Figure 1:
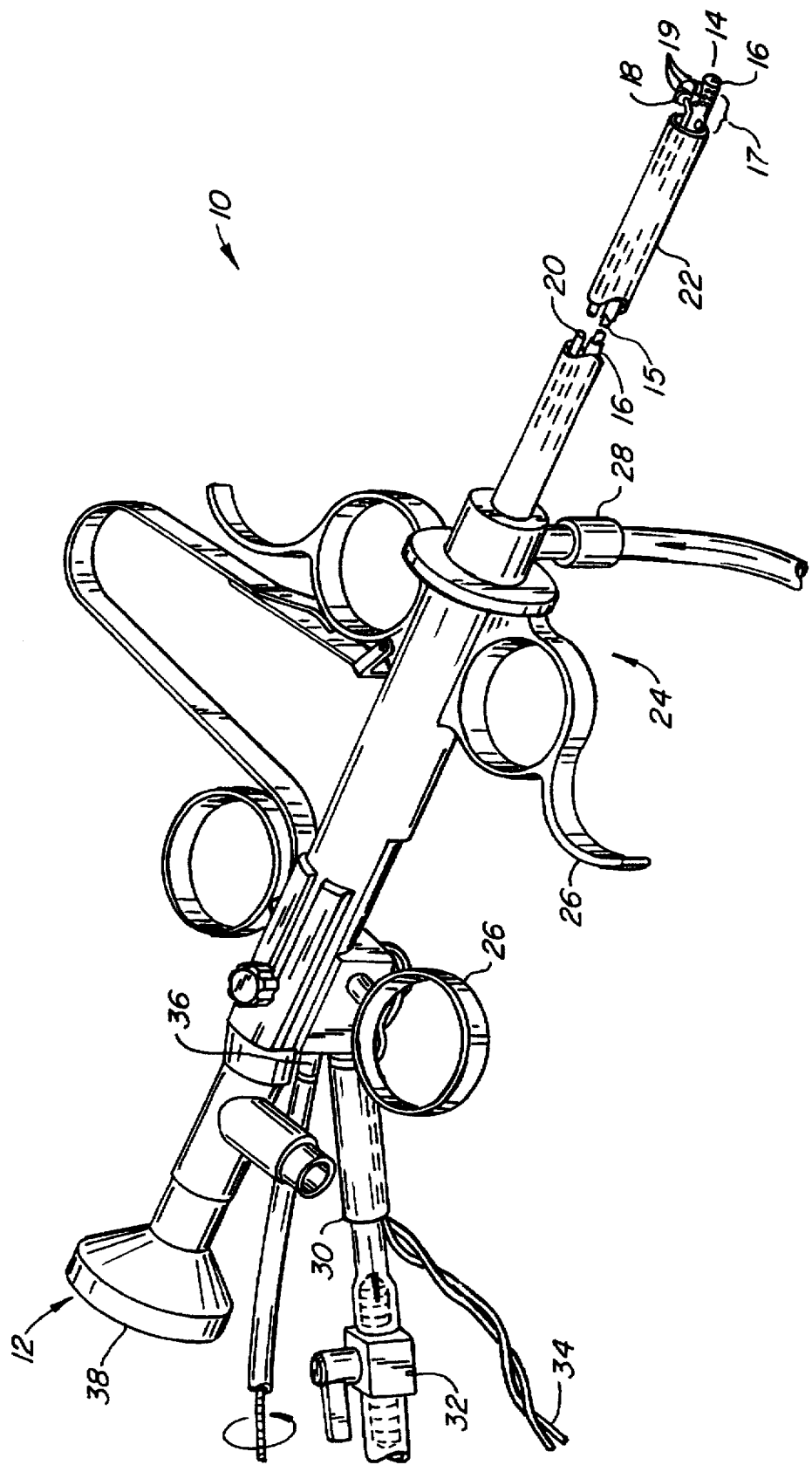
FIG. 1 is a perspective view of a resection probe according to the principles of the present invention, showing a proximal handle and several of the probe system connections.

Referring now to FIG. 1, resection probe 10 generally has a proximal end 12 and a distal end 14. An inner tubular cutter member 15 is rotatably mounted within an outer tubular cutter member 16, together forming a chopping mechanism or "morcellator" for reducing the size of resected tissues and removing the tissues from an internal surgical site. Each of the structures includes an aperture near distal end 14, the apertures being axially aligned with each other so that tissues which protrude into the lumen of the outer tube are sheared by the rotating inner tube. This exemplary probe also includes an electrosurgical cutting surface 18 with a plurality of rolling elements 19. Fiber-optic imaging scope 20 is distally oriented toward cutting surface 18, and runs proximally within a sheath 22. Passages 17 through the wall of outer tube 16 are visible near distal end 14.

A probe handle housing 24 includes an actuation handle 26 for axially translating the shaft and cutting surface relative to the sheath. An irrigation fluid port 28 and aspiration removal port 30 generally provide a flow path for a clear, non-conductive fluid such as sorbitol-mannitol, mannitol, glycine, or the like. Alternatively, a conductive fluid may be used, for example, with bipolar electrosurgical devices and methods (as more fully explained in co-pending U.S. patent application Ser. No. 08/678,412, filed Jul. 2, 1996, the full disclosure of which is incorporated herein by reference), or when relying on mechanical cutting without electrosurgery.

Aspiration flow is controlled by an aspiration valve 32, so that the distension pressure may be maintained independently from flow. Electrosurgical connector wires 34 and a flex drive input 36 provide external electrical and mechanical power. An optical image eyepiece 38 is removably attached to housing 24 to optically direct the resection procedure. Optionally, an ultrasound transceiver may be mounted on the distal end of the probe. Such a distal ultrasound transducer may optionally comprise a one- or two-dimensional phased array to allow scanning of the resection tissue independent of any mechanical movement of the transducer or probe.

Figure 2:
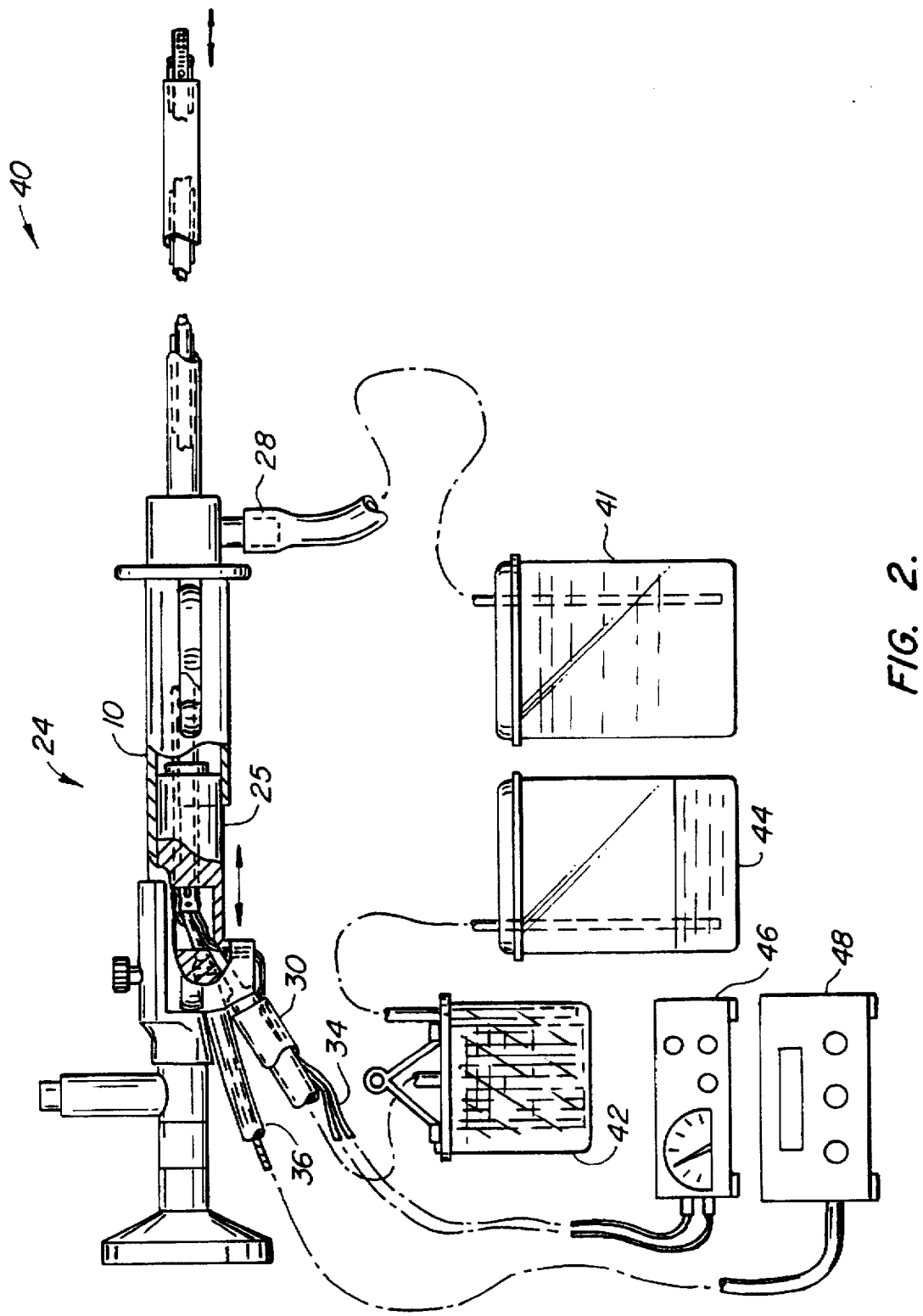
FIG. 2 illustrates a resection probe system, including the probe of FIG. 1.

Referring now to FIG. 2, a resection system 40 utilizes the input and output connectors on the housing of probe 10, together with standard stand-alone surgical system components, to minimize cost, weight, and fatigue when using probe 10 in a resection procedure. An irrigation supply 41 is connected to irrigation port 28 to provide a continuous flow of irrigation fluid during resection. Preferably, irrigation supply 41 comprises a standard irrigation supply bag suspended above the surgical site to provide a constant pressure gravity feed, allowing distension pressure to be varied simply by changing the height of the irrigation supply. Alternatively, a valve or controlled flow pump may be used to supply irrigation fluid.

In the exemplary embodiment, aspiration, mechanical rotation, and electrosurgical potential are coupled to the shaft through a disposable cartridge 25 on shaft housing 24, the disposable cartridge reciprocating with the shaft as shown. This disposable cartridge structure facilitates replacement of the cutting wire/shaft assembly (including the inner and outer tubes of the chopping mechanism) which would otherwise limit probe life. Fluid which leaves aspiration removal port 30 is directed through a filter canister 42 and then to an aspiration sump 44. Filter 42 removes the solid tissue fragments from the aspiration fluid for analysis. Sump 44 is preferably connected to a standard vacuum supply line to promote the withdrawal of aspiration fluid through the probe. Aspiration vacuum control is conveniently provided by aspiration valve 32 (see FIG. 1).

Mechanical power is supplied to flex drive input 36 by drive motor 48. Drive motor 48 preferably rotates at least in the range between 500 and 1500 rpm, and typically allows for rotation in either direction, or oscillating rotation back and forth. The morcellator generally shears tissue mechanically, without electrosurgical potential, although such potential may be advantageous for some embodiments of tubular surgical cutters.

The morcellator promotes aspiration of larger tissue fragments without clogging the aspiration flow path. The size of the morcellator can be reduced by breaking up tissue fragments with round or star shaped rollers 19, as more fully explained in co-pending U.S. patent application Ser. No. 08/705,229, filed Aug. 29, 1996 (Attorney Docket No. 16944-001210), the full disclosure of which is incorporated by reference. Often times, such rollers will be used to vaporize a significant amount of the resected tissue, as described in co-pending U.S. patent application Ser. No. 08/732,033, filed Oct. 16, 1996 (Attorney Docket No. 16944-000170), the full disclosure of which is also incorporated by reference. Nonetheless, the presence of the morcellator is generally advantageous to aspirate tissue fragments which are released.

Controlled electrosurgical power is supplied through electrosurgical wires 34 to the cutting member by power unit 46. As is more fully described in co-pending U.S. application Ser. No. 08/705,228, filed Aug. 29, 1996, (Attorney Docket No. 16944-001110) also incorporated by reference, a switch (not shown) optionally allows application of electrosurgical power to be directed to a roller mounted distally of the aperture (not shown). Irrigation flow is directed distally over the scope through the sheath, and the aspiration flow returns proximally (with the severed tissue fragments) through the lumen of the cooperating tubular cutters, as more fully described in co-pending U.S. patent application Ser. No. 08/542,289, the full disclosure of which is herein incorporated by reference.

Figure 3:
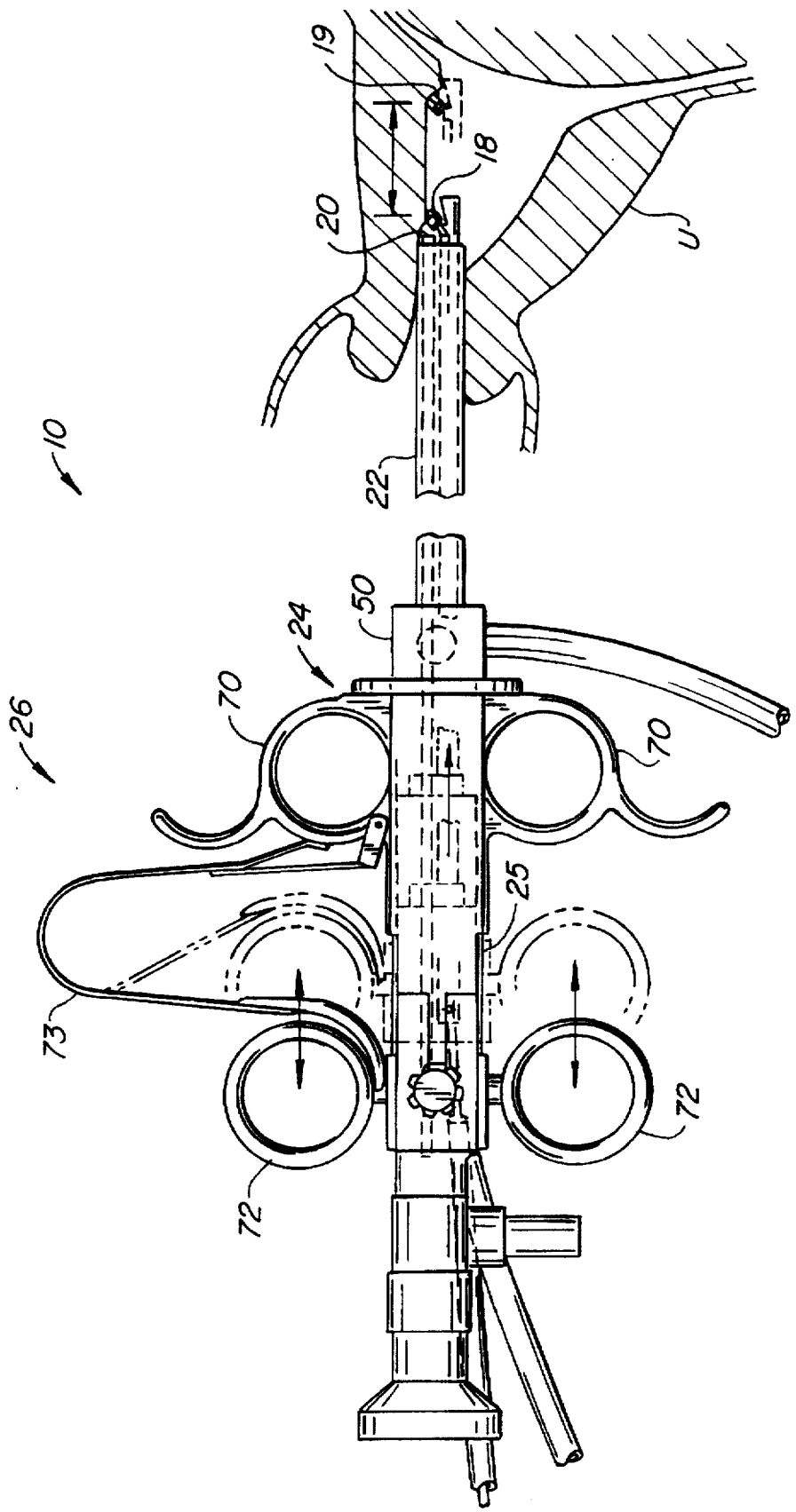
FIG. 3 illustrates a method of use of the probe of FIG. 1 for trans-cervical fibroid removal from the uterus.

Referring to FIG. 3, an exemplary method for using resection probe 10 typically comprises transcervically introducing sheath 22 into the uterus U. Such insertion is facilitated by use of an obturator. Manipulation of the probe is facilitated by limiting the sheath to a maximum of about 27 Fr (about 9 mm in diameter). Once the sheath is properly positioned, the obturator is removed and the cutting member 18 and scope 20 are inserted through the sheath and proximal housing 24 is attached to sheath coupling 50.

The probe is manipulated from the proximal housing 24 using articulation handle 26. The surgeon inserts the fingers of one hand through finger handle 70, and inserts the thumb of the same hand through thumb ring 72. Preferably, the fingers are held stationary while the thumb ring extends the shaft and cutting member distally from the sheath. Thumb ring 72 is biased toward the proximal direction, so that removal of strips of tissue typically takes place under the assistance of biasing spring 73.

Removal of fibroid tissue from the uterus U begins with the cutting member 18 extended distally from the sheath 22 and energized with RF power, as described above. As illustrated in FIG. 3, the shaft is generally aligned with the tissue to be removed so that proximally actuating thumb ring 72 draws electrosurgical cutting surface 18 through fibroid and/or endometrial tissue. The procedure is directed using scope 20, preferably while the scope and sheath are held substantially motionless using finger handle 70. Performing each cut towards the viewing scope helps to avoid inadvertently perforating uterus U.

In an alternative embodiment of the method of the present invention, the surgeon may manipulate the thumb ring relative to the finger handle to bring the cutting surface 18 to a preferred viewing distance from scope 20, and then translate the shaft and housing assemblies together proximally. This provides a longer cutting stroke for cutting surface 18, and decreases the time required for the resection procedure.

As the electrosurgical cutting surface 18 moves proximally, rolling elements 19 generally roll against the fibroid or endometrial tissue. These rolling elements fan outward radially, so that multiple separate fibroid tissue segments are detached from the uterus by each stroke of the cutting member. Therefore, the detached tissue segments are each smaller than an equivalent single strip of severed tissue, and are significantly easier to draw into the morcellator for extraction. The cutting member can thus have an increased axial projection area, i.e., can remove a greater volume of tissue with each stroke, without overwhelming the morcellator. Those of skill in the art will appreciate that such methods and devices will have many advantageous applications, including for the removal of selected thoracic tissues, particularly lung tissue, tissues of the bladder, and tissues of the prostate.

Referring now to FIGS. 4 and 5, the chopping action of the tubular surgical cutters provided by rotating inner tube 15 within a lumen 80 of outer tube 16. Each of the inner and outer tubes includes an aperture 82 having a cutting edge 84. When these apertures are aligned and distal end 14 moves radially against a target tissue, the tissue will protrude through the aligned apertures and into a lumen of the inner tube 86. However, as inner tube 15 rotates, the aperture of the outer tube is blocked off by the structure of the inner tube and tissue fragments protruding into the lumen of the inner tube are sheared between cutting edges 84 of the two apertures.

As can be understood with reference to FIG. 4, once the structure of the inner tube completely blocks the aperture of outer tube 16, the tissue fragment has been severed and is ready for transport proximally through lumen 86 of inner tube 15. However, if the only path for aspiration flow proximally through lumen 86 is provided by the cutting apertures, that flow will be substantially blocked momentarily after the tissue has been severed. This impedes transportation of the severed tissue fragments proximally, and would also allow the vacuum within the transportation lumen to build if no other aspiration flow ports were provided. Hence, if no aspiration flow ports 17 are provided, the full force of the vacuum would again be directed through the severing apertures once they came back into alignment. This laterally directed vacuum through the aligned severing apertures may draw a flexible target tissue against the outer surface of outer tube 16 so as to completely block flow through the aperture. A high level of vacuum may draw softer, more compressible tissue into lumen 86 of the inner cutter tube. Under certain combinations of tissue softness and vacuum, a plug of tissue can be drawn into the inner lumen 86 and severed. This plug can block the inner lumen, preventing further tissue aspiration.

To avoid the build up of vacuum within the tubular surgical cutter, and to ensure aspiration flow continues throughout the rotation of inner tube 15, aspiration flow ports 17 provide an open aspiration fluid path, both when the apertures are in open alignment, and after the severing stroke when inner tube 15 substantially blocks the aperture of the outer tube 16. Specifically, vacuum relief ports 88 on the inner and outer tubes are aligned to provide open fluid communication to lumen 86 when the apertures 82 are also aligned. Hence, vacuum relief ports 88 provide an open aspiration path directed away from the target tissue to reduce the vacuum at the time the vacuum has its greatest influence on the tissue at cutting aperture 84, to prevent excessively large tissue fragments from being drawn into the aligned apertures, and to ensure that aspiration flow continues even if flow through the apertures is blocked by the surrounding tissue.

Additionally, a plurality of fenestrations 90 through the structure of outer tube 16 align with aperture 84 of inner tube 15, providing an alternative flow path when the inner tube structure blocks fluid flow through the aperture of the outer tube. This helps provide aspiration flow after the cutting stroke is complete, to promote proximal transportation of the severed tissue fragment within lumen 86 of inner tube 15.

It should be recognized that in some embodiments only one of these two types of aspiration flow control ports will be desired. For example, some embodiments of surgical tubular cutters may benefit from application of the full vacuum force through the aligned severing apertures, so that vacuum relief ports are not desired, but will still make use of fenestrations to promote transportation of the tissue fragments after they have been severed.

Figure 6:
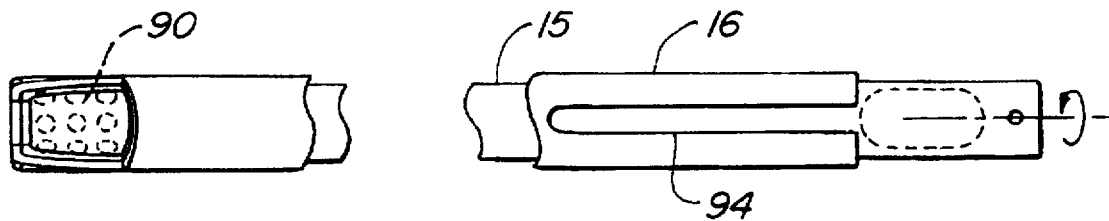
FIG. 6 is a plan view of the proximal and distal ends of the inner and outer tubes of FIG. 4.
Figure 7:
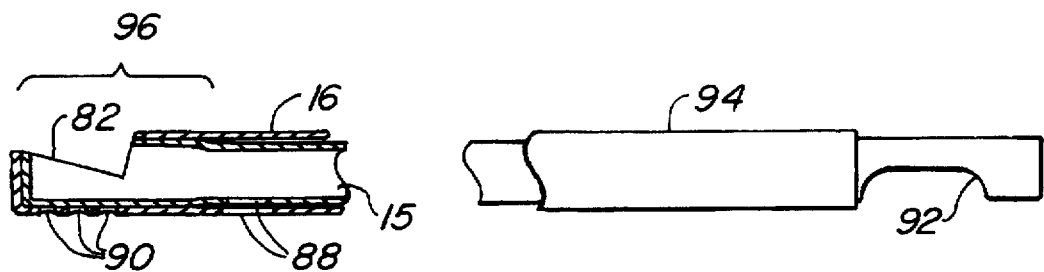
FIG. 7 is a partial cross-sectional side view of the inner and outer tubes of FIG. 4.

Referring now to FIGS. 6 and 7, the intermittent nature of the aspiration flow paths provided by vacuum relief ports 88 and fenestrations 90 can be understood. At some radial positions during rotation, the structure of inner tube 15 will block these aspiration flow ports, so that they are open only intermittently during the rotating severing stroke. Alternative aspiration flow control ports could be provided which are open continuously throughout the rotation of inner tube 15, but such continuously open ports are particularly subject to clogging by any loose tissue fragments within the area of the surgical site. Nonetheless, aspiration flow control ports which are "at least intermittently open" (that is, which are either continuously open or intermittently open during the rotation of the inner tube) are within the scope of the present invention.

Also illustrated in FIGS. 6 and 7 are the proximal discharge port 92 which allow removal of the aspirated tissue fragments from the lumen of the inner tube, and a proximal slot 94 which facilitates mounting the outer tube 16 in a fixed rotational position relative to the proximal housing of the probe. A distal tight tolerance region 96 improves the shearing action between the cooperating apertures 82, reduces entrapment of tissue fragments between the inner and outer tubes, and also decreases friction during rotation of the inner tube.

Figure 8:
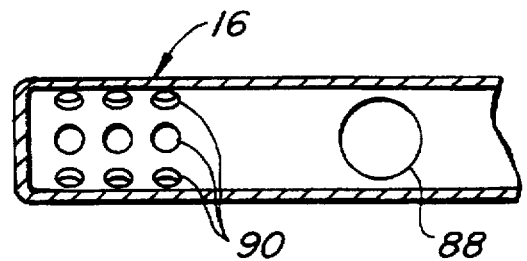
FIG. 8 is a cross-sectional view from above of the outer tubular surgical cutter of FIG. 4.

FIG. 8 illustrates the pattern of fenestrations 90 through outer tube 16, and indicates the relative sizes of an exemplary suction relief port 88 relative to those fenestrations.

Although the specific embodiments have been described in some detail, by way of illustration and for clarity of understanding, a variety of modifications, adaptations, and alternatives will be obvious to those of skill in the art. For example, it may be possible in some embodiments to provide fenestrations through the structure of the inner tube opposite its aperture, which allow flow to occur through the aperture of the outer tubular cutter aperture after the cutting stroke. Hence, the scope of the present invention is limited solely by the appended claims.

What is claimed is:

1. A tubular surgical cutter comprising:
    an outer tubular structure having a proximal end, a distal end, a cutting edge which borders an aperture disposed near the distal end, a lumen between the aperture and the proximal end, and at least one aspiration flow port near the distal end; and
    an inner tubular structure rotatably disposed within the lumen of the outer tube, the inner tube having a proximal end, a distal end, a lumen between the distal end and the proximal end, and a cutting edge which cooperates with the cutting edge of the outer tube to sever tissue fragments which enter the aperture of the outer tube when the inner tube rotates;
    wherein the at least one aspiration flow port is in at least intermittent fluid communication with the lumen of the rotating inner tube, and wherein the at least one aspiration flow port admits sufficient aspiration flow to transport the severed tissue fragments proximally through the lumen of the inner tube when aspiration flow through the aperture is blocked.

2. A tubular cutter as claimed in claim 1, wherein the at least one aspiration flow port is radially separated from the aperture of the outer tube to avoid blockage of the aspiration flow port by the target tissues.

3. A tubular cutter as claimed in claim 2, wherein the inner tube comprises a vacuum relief port, and wherein the at least one aspiration flow port comprises a vacuum relief port which aligns intermittently with the vacuum relief port on the inner tube to reduce tissue fragment sizes.

4. A tubular cutter as claimed in claim 3, wherein the vacuum relief port of the outer tube is roughly opposite the aperture on the outer tube.

5. A tubular cutter as claimed in claim 1, wherein the at least one aspiration flow port is in open fluid communication with the lumen of the inner tube when the outer aperture is at least partially blocked by the inner tube.

6. A tubular cutter as claimed in claim 5, wherein the at least one aspiration flow port comprises a plurality of fenestrations which are in fluid communication with the lumen of the inner tube when the aperture of the outer tube is blocked by the inner tube.

7. A tubular surgical cutter comprising:

an outer tubular structure having a proximal end, a distal end, a cutting edge which borders an aperture disposed near the distal end, a lumen between the aperture and the proximal end, and a vacuum relief port disposed near the distal end and in fluid communication with the lumen; and an inner tubular structure having a proximal end, a distal end, a cutting edge which borders an aperture disposed near the distal end, a lumen between the aperture and the proximal end, and a vacuum relief port disposed near the distal end and in fluid communication with the lumen;

wherein the inner tube is rotatably disposed within the lumen of the outer tube so that the cutting edges cooperate to sever tissue fragments which protrude into the apertures, and wherein the vacuum relief ports are separated from the apertures and aligned with each other when the apertures are aligned to draw fluid into the lumen of the inner tube with the tissue fragments.

8. A tubular surgical cutter as claimed in claim 7, further comprising an electrosurgical cutter disposed near the distal end of the outer tube for removing strips of tissue from an internal surgical site.

9. A tubular surgical cutter as claimed in claim 8, wherein the cutter is disposed adjacent the aperture of the outer tube and roughly opposite the vacuum relief port of the outer tube so that the strips of tissue are removed through the apertures and clogging of the vacuum relief port is avoided.

10. A tubular surgical cutter comprising:

an outer tubular structure having a proximal end, a distal end, a cutting edge which borders an aperture disposed near the distal end, a lumen between the aperture and the proximal end, and a plurality of fenestrations disposed near the distal end and in fluid communication with the lumen; and an inner tubular structure having a proximal end, a distal end, an aperture, a cutting edge disposed near the distal end, and a lumen between the aperture and the proximal end;

wherein the inner tube is rotatably disposed within the lumen of the outer tube so that the cutting edges cooperate to sever tissue fragments which protrude into the aperture of the outer tube, and wherein the fenestrations align with the aperture of the inner tube when the inner tube blocks flow through the aperture of the outer tube to draw fluid into the lumen of the inner tube after the tissue fragments have been severed.

11. A tubular surgical cutter as claimed in claim 10, further comprising an electrosurgical cutter disposed near the distal end of the outer tube for removing strips of tissue from an internal surgical site.

12. A tubular surgical cutter as claimed in claim 11, wherein the cutter is disposed adjacent the aperture of the outer tube and roughly opposite the fenestrations of the outer tube so that the strips of tissue are removed through the apertures and clogging of the fenestrations is avoided.

13. A method for removing tissue from an internal surgical site comprising:

irrigating the site with fluid;

aspirating fluid from the site by drawing the fluid into an aperture and through a lumen of a tube;

protruding a target tissue at the site into the aperture;

severing a tissue fragment from the target tissue by rotating an inner cutting edge within the aperture;

drawing sufficient fluid into the lumen through an aspiration port of the tube to transport the severed tissue fragments proximally through the lumen of the when fluid flow through the aperture is blocked by the target tissue.

* * * * *